United States Patent
Riley et al.

Patent Number: 5,672,155
Date of Patent: Sep. 30, 1997

[54] FLUID TRANSFER APPARATUS

[76] Inventors: Robert Q. Riley, 6835 E. Sheena Dr., Scottsdale, Ariz. 85254; Thomas J. Aksamit, 3222 E. Oregon Ave., Phoenix, Ariz. 85018

[21] Appl. No.: 662,226

[22] Filed: Jun. 14, 1996

[51] Int. Cl.$^6$ .................................................. A61M 5/24
[52] U.S. Cl. ........................ 604/154; 604/131; 604/152; 604/155
[58] Field of Search .......................... 604/65–67, 131, 604/154–156; 128/DIG. 1

[56] References Cited

U.S. PATENT DOCUMENTS

| | | |
|---|---|---|
| 2,702,547 | 2/1955 | Glass . |
| 3,415,419 | 12/1968 | Jewett et al. . |
| 3,858,581 | 1/1975 | Kamen ............................. 604/155 |
| 3,997,084 | 12/1976 | Davis, Jr. .......................... 222/326 |
| 4,006,736 | 2/1977 | Kranys et al. .............. 128/DIG. 1 X |
| 4,108,177 | 8/1978 | Pistor ................................ 604/155 |
| 4,335,834 | 6/1982 | Zepkin ................................ 222/63 |
| 4,426,024 | 1/1984 | Hogan et al. ...................... 604/141 |
| 4,429,724 | 2/1984 | Dorros et al. ..................... 604/920 |
| 4,529,401 | 7/1985 | Leslie et al. ...................... 604/131 |
| 4,731,058 | 3/1988 | Doan ................................. 604/155 |
| 4,787,893 | 11/1988 | Villette ............................. 604/154 |
| 5,034,003 | 7/1991 | Denance ........................... 604/155 |
| 5,139,484 | 8/1992 | Hazon et al. ..................... 604/154 |
| 5,269,762 | 12/1993 | Armbruster et al. ............. 604/155 |
| 5,322,511 | 6/1994 | Armbruster et al. ............. 604/155 |
| 5,368,572 | 11/1994 | Shirota ............................. 604/154 |

FOREIGN PATENT DOCUMENTS

| | | |
|---|---|---|
| 0 375 584 | 6/1990 | European Pat. Off. . |
| 2390-175 | 1/1979 | France . |
| 3-99231 | 9/1991 | Japan . |

*Primary Examiner*—Sam Rimell
*Assistant Examiner*—Robert V. Racunas
*Attorney, Agent, or Firm*—Parsons & Goltry; Robert A. Parsons; Michael W. Goltry

[57] ABSTRACT

A body having a syringe receptacle for receiving and retaining a syringe having a plunger, a housing containing a drive assembly for moving the plunger of the syringe between a depressed position and an extended position, a grip containing a control assembly for controlling the operation of the drive assembly in programmable modes of operation.

22 Claims, 6 Drawing Sheets

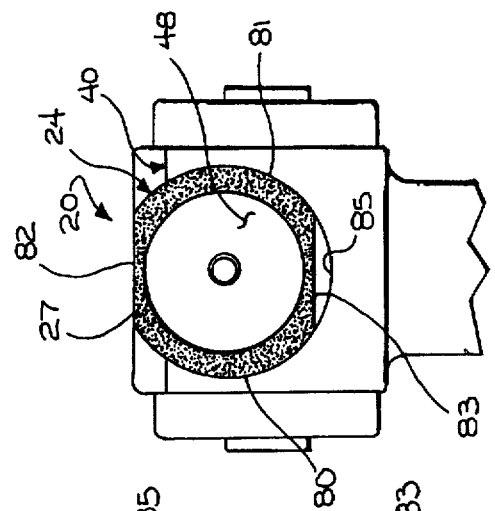
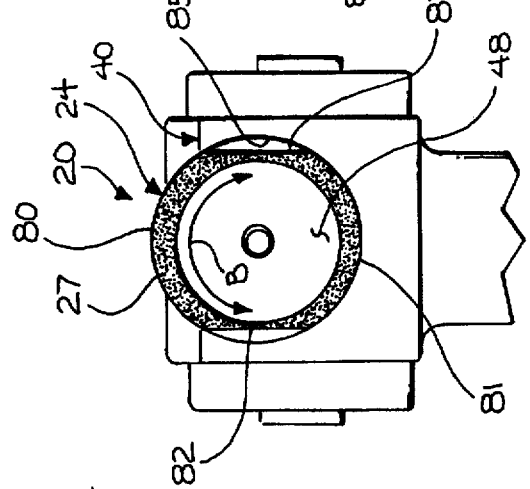
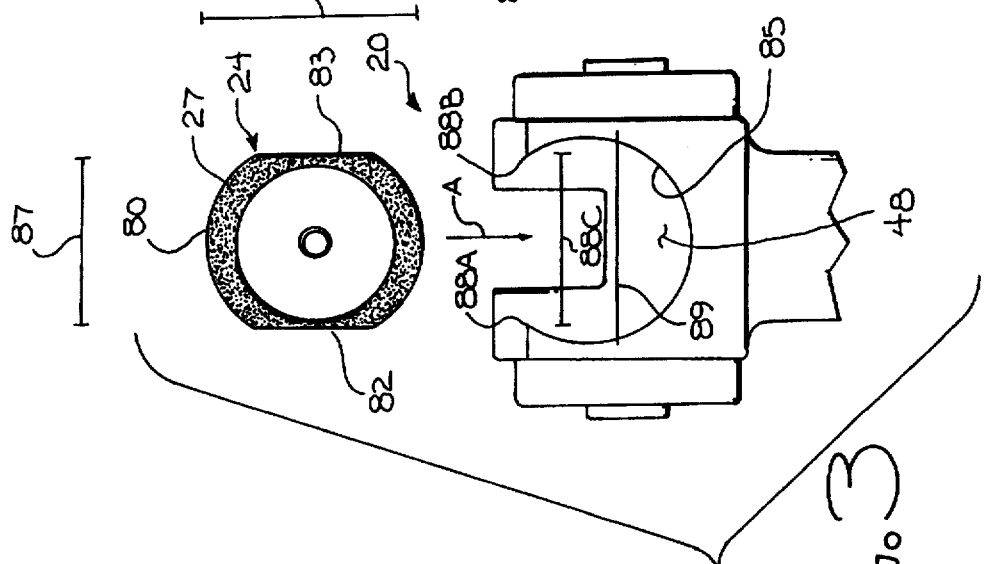

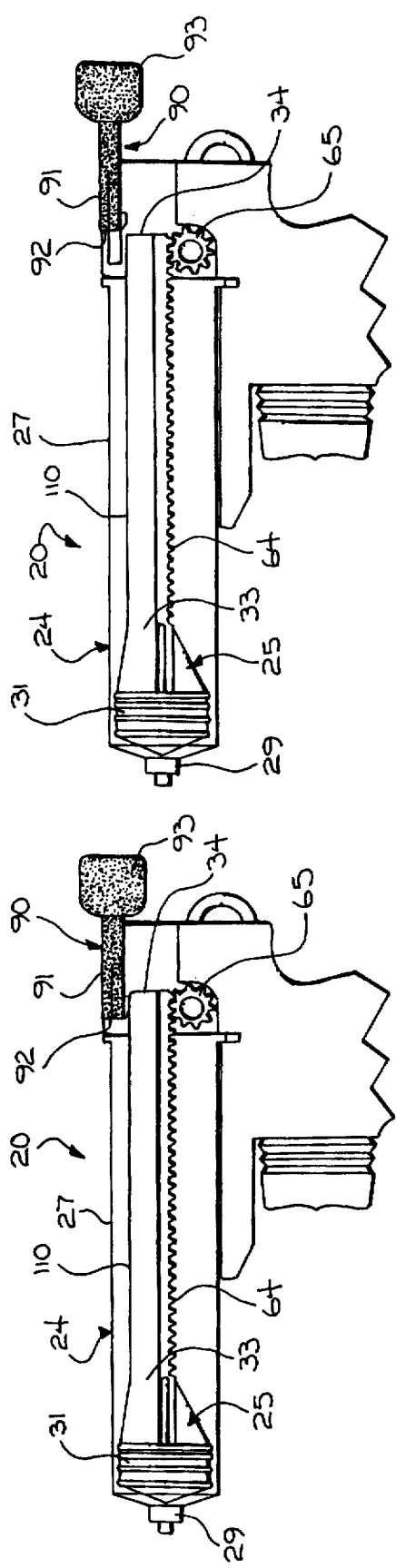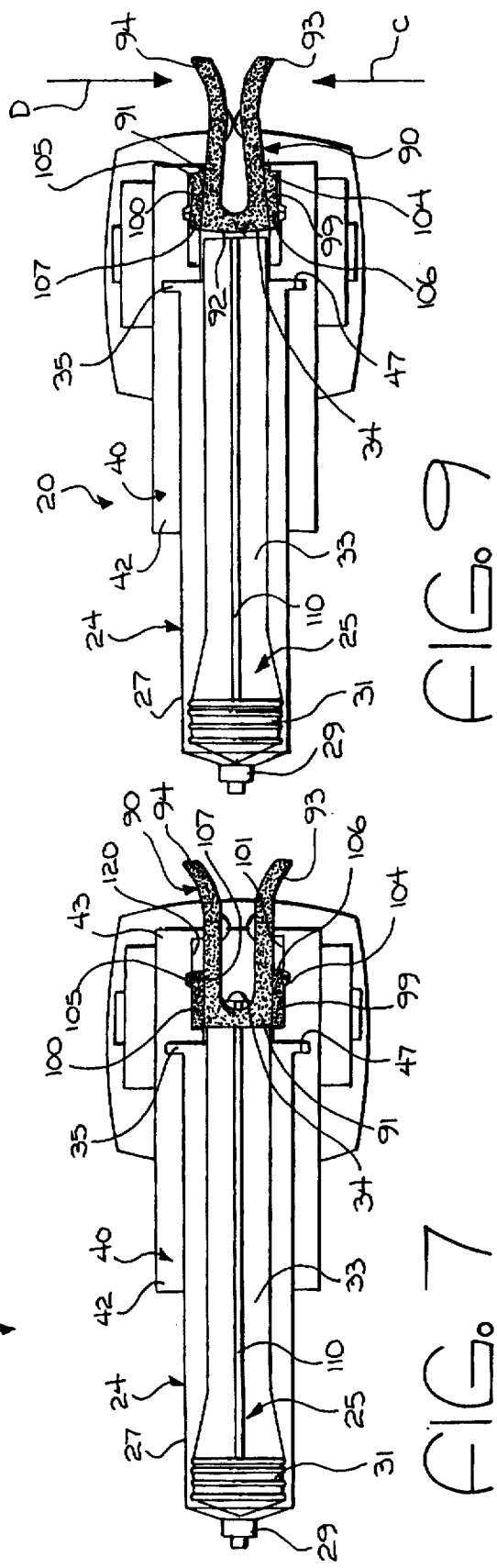

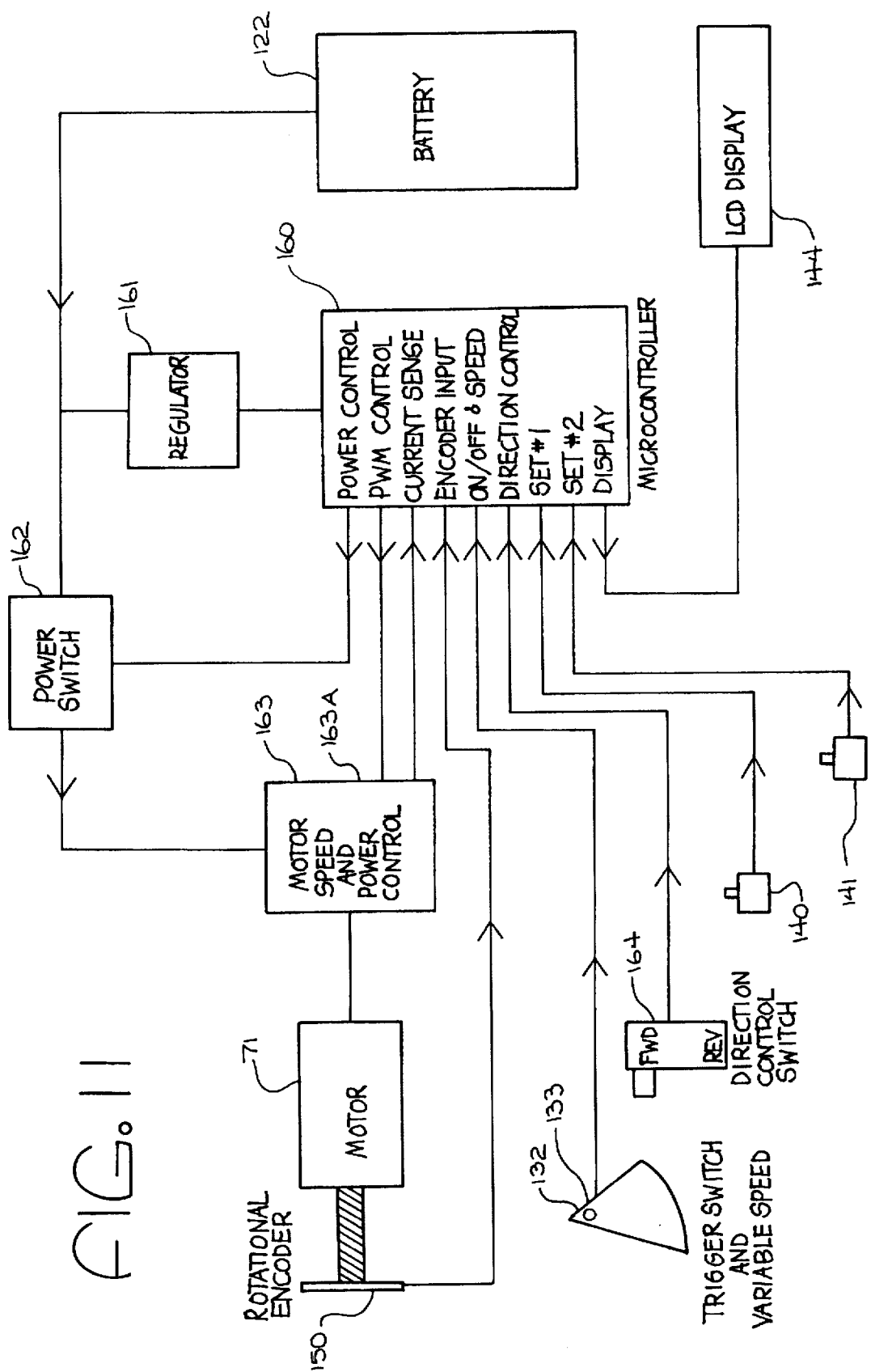

FLUID TRANSFER APPARATUS

BACKGROUND OF THE INVENTION

1. Field of the Invention

The present invention relates to devices for transferring fluids.

More particularly, the present invention relates to devices for aseptically transferring fluids.

In a further and more specific aspect, the present invention relates to a device for aseptically transferring fluids, the device having a plurality of programmable modes of operation.

2. Prior Art

Transfer of fluids has long been necessary for many different industries and applications. Some transfers can be accomplished simply by pouring the fluids from one container to another. Other fluid transfers require the transfer of specific amounts of fluid. Measuring devices such as graduated cylinders may be used to adequately measure the desired volume of fluid.

Some fluids, however, require a more aseptic transfer. This is especially true for fluids having medical applications. In medical applications, syringes have long been used to transfer fluids from storage containers such as vials and bottles to receiving containers which may be other storage containers or application containers such as elastomeric infusion pumps or medication cassettes. The syringe is inserted into the container, the syringe plunger is pulled back withdrawing a desired amount of fluid from the storage container. The syringe is then inserted into the receiving container and the plunger depressed, injecting the fluid. While this works well for transferring fluids to very small quantities of small receiving containers, when larger volumes of fluid are transferred or fluid is transferred to a larger number of receiving containers, problems appear.

When a large volume of fluid must be transferred, a large syringe is required. This can present difficulties for people with small hands. The force required to be applied to the syringe, especially in larger syringes during manual transfer of fluids, can result in fatigue of hands and muscles slowing the process. Repetition of the filling and emptying of a syringe can be tiring, causing errors, spillage, or contamination of the fluids. Aseptic techniques must be followed to prevent contamination of the fluids. Fatigue can result in aseptic techniques not being followed precisely. Furthermore, manual use of a syringe for transfer often results in touching of the syringe plunger and plunger shaft, requiring disposal of the syringe after a single use, or increased chance of contamination.

To overcome some of these problems, various devices have been developed. Large stationary electronic pumps designed for repetitive dispensing and reconstituting of medications are used for transferring large batches of fluids. These devices are generally stationary, since they tend to be bulky and difficult to set up. Some can measure the amount of fluid transferred, but require calibration before each such procedure. Once set up and calibrated, these devices are very well adapted to repetitious transfer of large batches of fluid, avoiding fatigue and repetitive motion problems in the hands of the user. However, since these devices are stationary, they tend to be inconvenient for small run use, and are typically very expensive, complex, and difficult to set up. If various accessories are used, such as a filter, calibration can be skewed, with the amount dispensed inaccurate.

Much less complex and easier to use devices have been developed employing a syringe for transferring fluid. Some of these devices can be used without the user touching the plunger or plunger shaft, thereby allowing repetitive use of a single syringe. However, these devices still require the manual depression or withdraw of the plunger to inject or take up fluids.

It would be highly advantageous, therefore, to remedy the foregoing and other deficiencies inherent in the prior art.

Accordingly, it is an object of the present invention to provide an improved method of transferring fluids.

Another object of the present invention is to provide a fluid transfer apparatus which is relatively inexpensive to manufacture and use.

And another object of the present invention is to provide a fluid transfer apparatus which is highly versatile, being able to provide a variety of functions.

Still another object of the present invention is to provide a fluid transfer device which employs calibrated syringes for accurate measurement of fluids.

Yet another object of the present invention is to provide a fluid transfer apparatus which is compact and easily used in small work areas.

Yet still another object of the present invention is to provide a fluid transfer apparatus which is mobile for convenience and not restricted to a specific location.

And a further object of the present invention is to provide a fluid transfer device which can be easily calibrated by the user.

Still a further object of the immediate invention is to provide a fluid transfer apparatus that is programmable having a plurality of modes of operation.

Yet a further object of the invention is the provision of inhibiting fatigue in a user when transferring fluids over an extended period of time.

And still a further object of the invention is to provide a fluid transfer apparatus that is self adjustable for inhibiting the drawing of air either into or out of a fluid being transferred.

Yet a further object of the present invention is to provide a fluid transfer apparatus which can be used to reconstitute lyophilized powder in vials and to withdraw the right constituted powder for dispensing into other containers.

And yet a further object of the present invention is to provide a fluid transfer apparatus which is hand held and automatically transfers fluids.

SUMMARY OF THE INVENTION

Briefly, to achieve the desired objects of the instant invention in accordance with a preferred embodiment thereof, provided is a body for receiving a syringe having a plunger. The body includes a syringe receptacle having an outlet end and a rearward end. Further provided is a drive assembly including actuating means, for moving the plunger of the syringe between a depressed and extended position for injection of fluids and for uptake fluids respectively. The actuating means is preferably a motor coupled to the syringe plunger, controlled by the operator through control means. The syringe includes a barrel which is rotatably secured within a barrel cavity of the body. The fluid transfer device may further includes a sensor means for monitoring said motor and for preventing said motor from operative above a predetermined current consumption level, and a plunger lock for engaging the plunger with the drive assembly and for further securing the syringe in place within the body.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which:

FIG. 3 is a front plan view of the fluid transfer apparatus with the syringe shown prior to being inserted into a syringe cavity;

FIG. 4 is a front plan view very similar to the view of FIG. 3, with the syringe shown as it would appear inserted within the syringe cavity;

FIG. 5 is a front plan view very similar to the view of FIG. 4, with the syringe shown as it would appear in a secured configuration within the syringe cavity;

FIG. 6 is a fragmented side plan view of the fluid transfer apparatus with the syringe plunger shown in the depressed position, with the plunger lock shown engaged in a locked configuration;

FIG. 7 is a top plan view of the fluid transfer apparatus with the syringe plunger shown in the depressed position, with the plunger lock shown engaged in the locked configuration;

FIG. 8 is a fragmented side plan view of the fluid transfer apparatus with the syringe plunger shown in the depressed position, with the plunger lock shown disengaged in an unlocked configuration;

FIG. 9 is a top plan view of the fluid transfer apparatus with the syringe plunger shown in the depressed position, with the plunger lock shown disengaged in the unlocked configuration;

FIG. 11 is block diagram schematic representation of the electrical components associated with the mechanical elements of the fluid transfer apparatus.

DETAILED DESCRIPTION OF THE PREFERRED EMBODIMENT

Figure 1:
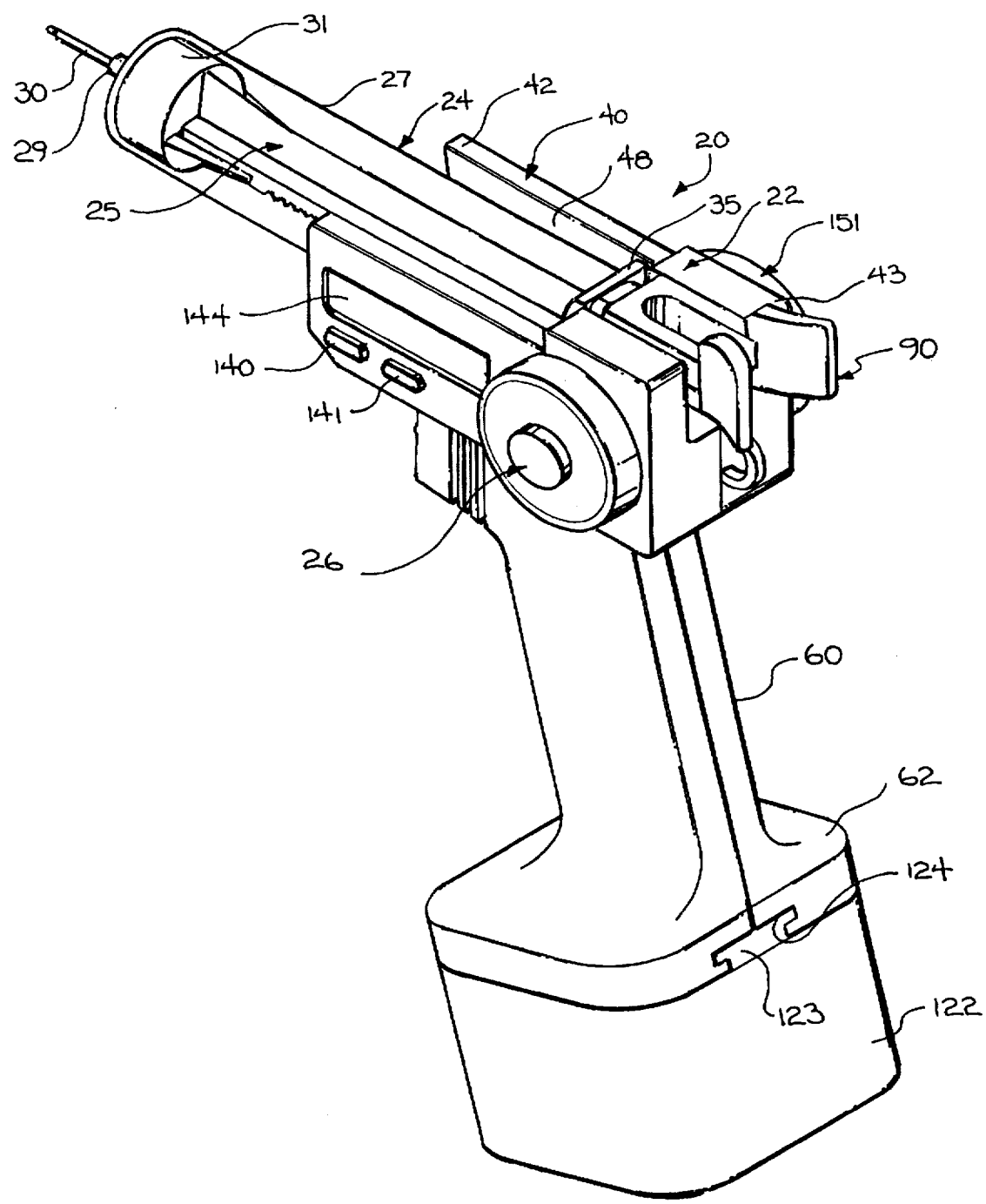
FIG. 1 is a perspective view of a fluid transfer apparatus, constructed in accordance with the teachings of the instant invention, as it would appear immediately prior to intake of fluid into a syringe, with a syringe plunger in the depressed position.

Turning now to the drawings in which like reference characters indicate corresponding elements throughout the several views, attention is first directed to FIG. 1 which illustrates a fluid transfer apparatus generally designated by the reference character 20. Fluid transfer apparatus 20 consists of a body 22 configured to be supported and operated by a hand of an operator. Body 22 receives a syringe 24, preferably a dedicated 60 cubic centimeter disposable syringe, having a plunger 25 moveable between a depressed and an extended position by a drive means, to be herein discussed, portions of which are housed within housing 26, which is in turn controlled by control means, details of which will be discussed as the detailed description ensues. Fluid transfer apparatus 20 is used primarily, but not exclusively, for transferring pharmacological fluids/ solutions from a storage vessel into a receiving vessel through the operation of powering syringe 24 through fill and dispense movements as selected by an operator. As will become apparent as the detailed description continues, fluid transfer apparatus 20 increases an operator's production of compounded solution, and relieves the operator of the stress and fatigue that normally results from manually operating a syringe.

Figure 2:
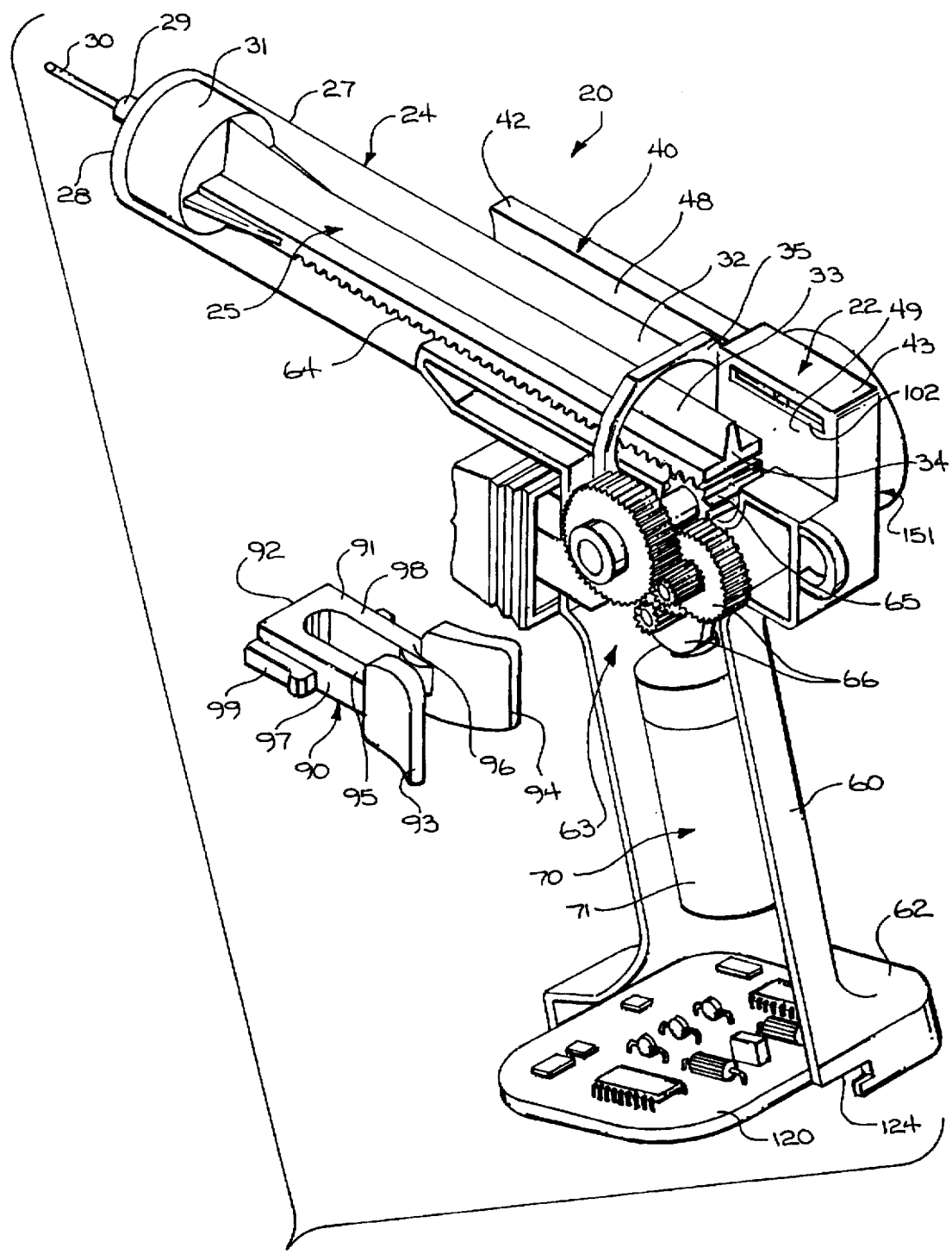
FIG. 2 is a partially exploded cutaway perspective view illustrating the internal components of the fluid transfer apparatus of FIG. 1, and further illustrating a plunger lock.

Referring to FIG. 2, syringe 24 may be a conventional syringe consisting of plunger 25 and a barrel 27 having an outlet end 28 terminating in a tip 29 to which various attachments, such as a needle 30, filters, tubing, or other appropriate attachments may be attached. A plunger receiving end 32 opposite outlet end 28 is configured to receive plunger 25. Plunger 25 includes a piston 31 closely fitted within barrel 27, and a plunger shaft 33 extending from the piston 31 and terminating in an end 34. A gripping flange 35 extends outward from barrel 27 proximate plunger receiving end 32.

Still referring to FIG. 2, with additional reference to FIG. 1, body 22 of fluid transfer apparatus 20 includes a syringe receiving receptacle 40 having an open outlet end 42 and an open rearward end 43. Syringe receiving receptacle 40 is generally trough shaped, defining a cavity. With momentary reference to FIG. 7, a slot 47 is formed in syringe receiving receptacle 40 intermediate outlet end 42 and rearward end 43, and is configured to receive gripping flange 35 of syringe 24. Slot 47 separates the cavity of syringe receiving receptacle 40 into a barrel cavity 48 proximate outlet end 42 and a plunger cavity 49 proximate rearward end 43. Syringe 24 is inserted into syringe receiving receptacle 40 with barrel 27 received by barrel cavity 48, tip 29 extending forwardly from outlet end 42, and gripping flange 25 inserted in slot 47. Plunger 25 is moveably received within and through plunger cavity 49. Those skilled in the art will understand that syringe receiving receptacle 40 is capable of receiving different size syringes.

With continuing reference to FIG. 2, body 22 further includes housing 26 formed proximate rearward end 43 and further located at a generally lateral position relative plunger cavity 49. Body 22 also includes a grip 60 extending downward from housing 26 under plunger cavity 49 and terminating with a lower housing 62. Also included is a drive assembly 63 including a plunger gear 64 formed along the underside of plunger 25 extending from end 34 to proximate piston 31, a pinion 65 housed beneath plunger gear 64 within housing 26 for engaging plunger gear 64, and an actuator means 70 which rotates pinion 65 in a clockwise or counter clockwise direction, moving plunger 25 reciprocatingly outwardly from rearward end 43 and outlet end 42. It will be readily understood by those having ordinary skill that other drive means may be used in combination with the instant invention as selectively desired without departing from the nature and scope of the instant invention as herein specifically described.

With continuing reference to FIG. 2, drive assembly 63 further includes a plurality of reduction gears 66, with a gear reduction of 325:1 for example, which couple actuator means 70, housed within grip 60, to a driven gear 68 coupled to pinion 65. With respect to the preferred embodiment, actuator means 70 is preferably comprised of an 12,000 RPM two way DC motor 71, although other motors may be used. As will be understood from FIG. 1 and FIG. 2, when syringe 24 is inserted into syringe receiving receptacle 40, with gripping flange 35 secured in slot 47, rotation of pinion 65 results in the depression and extension of plunger 25 within syringe 24.

Attention is now directed to FIGS. 3–4, illustrating the sequential steps of syringe 24 being inserted and secured within syringe receiving receptacle. In particular, as can be seen in FIG. 3, barrel 27 of syringe 24 includes opposing generally convex upper and lower surfaces, 80 and 81, and opposing generally planar side surfaces, 82 and 83. Barrel 27 includes an outer diameter defined by upper and lower surfaces 80 and 81, the outer diameter of barrel 27 defining a greater width 86. The area between side surfaces 82 and 83 defines a lesser width 87. As can be seen in FIG. 3, to insert barrel 27 into barrel cavity 48 of syringe receiving receptical 40, barrel 27 can be seen disposed in a configuration with side surfaces 82 and 83 disposed in a generally vertical configuration. Barrel 27 is then inserted within barrel cavity 48 of syringe receiving receptacle in the direction indicated by the arrowed line A, lower convex surfaced 81 coming to rest against plunger cavity 40. Plunger cavity 40 includes a substantially cylindrical configuration as defined by barrel cavity surface 85, and two spaced apart opposing upper lips 88A and 88B between which barrel 27 is inserted. The distance between lips 88A and 88B, defined as lip width 88C, is slightly greater than lesser width 87 so barrel 27 can be received therebetween, while still being less than greatest width 86.

Once received within barrel cavity 48 as can be seen in FIG. 4, barrel 27 is then rotated approximately 90 degrees in either the clockwise or counterclockwise direction, as indicated by the double arrowed line B, into a secured configuration. In the secured configuration, of which is shown in FIG. 5, convex surfaces 80 and 81 engage barrel surface 85 of barrel cavity 48, thus securing barrel 27 in place. Barrel cavity 48 includes a barrel cavity diameter which defines a barrel width 89 which is slightly greater than the diameter of barrel 27 and thus greatest width 86 for allowing barrel 27 to be received therein. Barrel 27 is secured in place within barrel cavity 48 as a result of not only substantial frictional engagement of convex surfaces 80 and 81 with barrel surface 85, but because lip width 88C is less than greatest width 86, barrel 27 is also prevented from removal between lips 88 and 89. Barrel 27 may be removed by reversing the above operation.

With attention directed back to FIG. 2, fluid transfer apparatus 20 further includes a plunger lock 90. Plunger lock 90 is preferably a unitary and horizontally actuated locking device for holding plunger gear 64 securely against pinion 65, and for further securing plunger 25 in place. Plunger lock 90, preferably constructed of a substantially flexible material such as plastic or the like, is generally comprised of a substantially U-shaped member 91 having a forward end 92, and outwardly extending handle elements, 93 and 94, extending from respective rearward ends, 95 and 96, of respective arms 97 and 98 of U-shaped member 91. With additional reference to FIG. 7, also included is are elements of an engagement set shown as generally laterally disposed tongue elements, 99 and 100 (tongue element 100 not shown in FIG. 2), configured to be received within respective complemental engagement elements of the engagement set shown as grooves, 101 (groove 100 not shown in FIG. 2) and 102, formed within plunger cavity 49.

In operation, plunger lock is movable between a locked or inserted position and an unlocked or detached position. In particular, plunger lock 90 is receivable within plunger cavity 49 by insertion into plunger cavity 49, with the respective tongue elements, 99 and 100, sized to be slidably received within the respective grooves, 101 and 102. In order to properly dispose plunger lock within plunger cavity 49, the respective handle elements, 93 and 94, are each manually urged inwardly in the directions indicated by the respective arrowed lines C and D shown in FIG. 9, with plunger lock 90 then urged inwardly into plunger cavity 49 for placement therein. When disposed inwardly into plunger cavity 49, the respective tongue elements, 99 and 100, slidably engage the respective grooves, 101 and 102, for guiding plunger lock 90 into plunger cavity 49. Furthermore, protrusions, 104 and 105, of which can further be seen in FIG. 2, extending outwardly from tongue elements, 99 and 100, respectively, engage notches, 106 and 107, formed within grooves, 101 and 102, respectively, thereby defining the plunger lock 90 in the locked configuration. This locked configuration is shown in FIG. 6 and FIG. 7. It will be readily appreciated by those having ordinary skill, that to detach or otherwise dispose plunger lock 90, herein described as the preferred locking means, in the unlocked position for removing plunger lock from plunger cavity 49 for allowing one to replace syringe 24, the above described operation need only be reversed.

With reference to FIG. 6, when locked in place within grooves 101 and 102, plunger lock 90 bears against a top edge 110 of plunger 25 for holding plunger gear 64 securely against pinion 65, and for holding plunger 25 in place, while still allowing plunger 25 to be extended and depressed. Furthermore, as can be seen in FIG. 8 and FIG. 9, plunger lock 90 is shown in the unlocked position.

With reference back to FIG. 2, lower housing 62 houses a circuit board 120. With additional reference to FIG. 1, carried directly beneath circuit board 120 is a battery 122, operative for supplying power to circuit board 120 and to drive assembly 63. Battery 122, preferably provided as a 9.6 volt battery, includes a tongue 123 sized to be removably received by groove 124 formed in lower housing 62 beneath circuit board 120. Circuit board 120 includes known electronic components operative for regulating and controlling syringe 24 through fill and dispense movements as desired by an operator.

Figure 10:
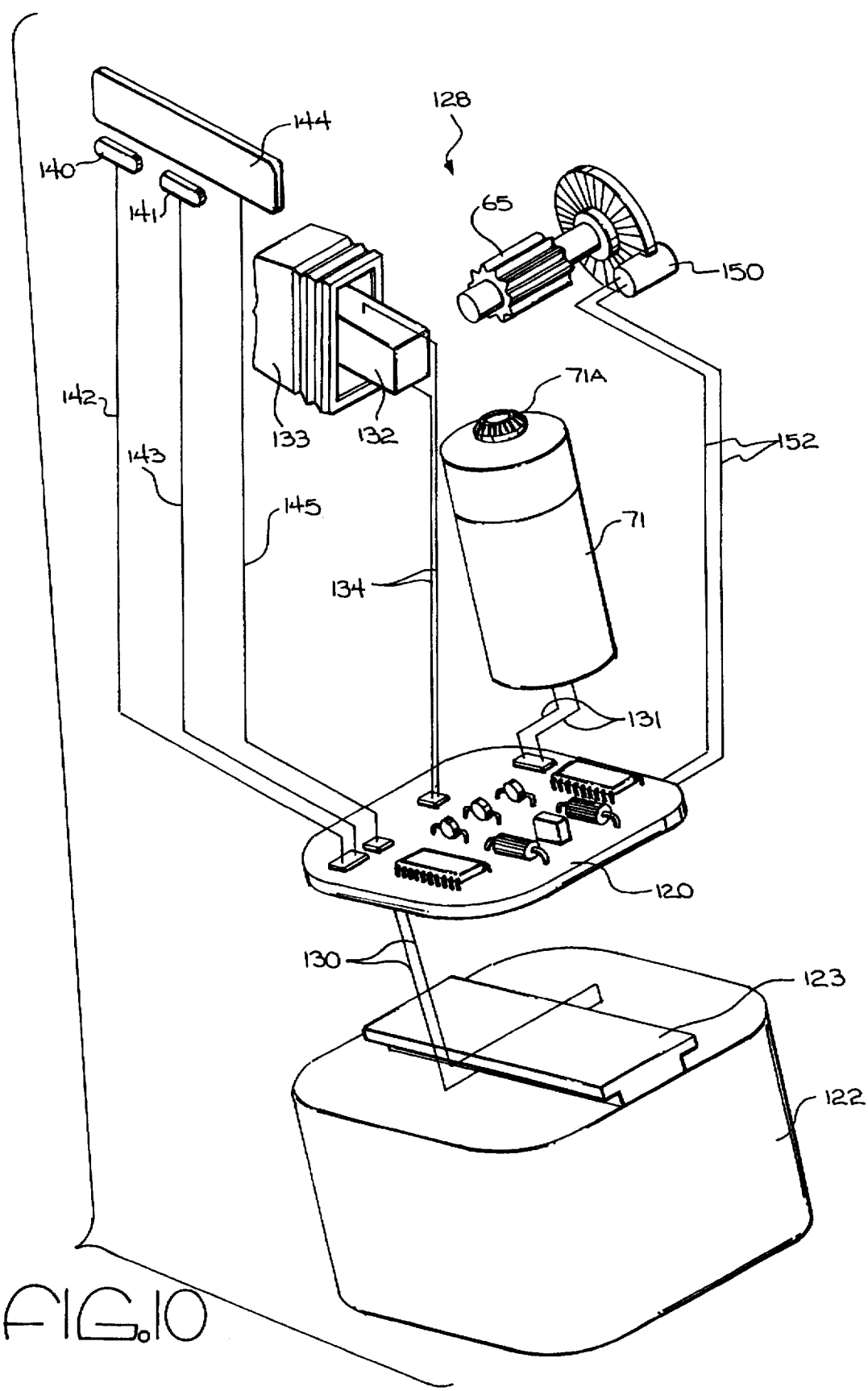
FIG. 10 is an exploded perspective schematic view of the electrical and mechanical components of the fluid transfer apparatus.

With reference to FIG. 10, shown is a preferred embodiment of a control assembly 128 for selectively controlling operation drive assembly 63 and for selectively controlling the operation of fluid transfer apparatus 20 in a plurality of programmable modes of operation. Although FIG. 10 illustrates the preferred control assembly, it will be readily appreciated by those having ordinary skill that other control means may be used. In particular, FIG. 10 illustrates an exploded perspective schematic view of the electrical and mechanical components of fluid transfer apparatus 20. As can be seen, circuit board 120 is electrically coupled to battery 122 via electrical interconnection 130, battery 122 being operative for providing power to control assembly 128. Power provided from battery 122 is then channeled through circuit board 120 to power the various electrical components of fluid transfer apparatus 20, of which will be immediately discussed.

Motor 71 is electrically coupled to circuit board 120 via electrical interconnection 131. Additionally, a switch 132 operated by a pivoting trigger 133 is electrically coupled to circuit board 120 via electrical interconnection 134. Switch 132 is preferably a variable-speed three way switch, one position operating motor 71 in a forward direction for depressing plunger 25 during a dispense movement, one position stopping motor 71, and one position reversing motor 71 for extending plunger 25 during a fill movement. The operation of motor 71, which further includes a drive gear 71A for driving reduction gears 66 which in turn actuate driven gear 68 previously discussed in combination with FIG. 2, through actuation of switch 132 by pivoting trigger 133 is controlled and regulated by circuit board 120, details of which will become readily apparent as the detailed description ensues. It will be understood that more sophisticated switches and motors known to those skilled in the art may be used, allowing variable speeds, depending upon how far trigger 133 is depressed.

As can be seen from FIG. 10, circuit board 120 is also electrically coupled to buttons 140 and 141 via electrical interconnections 142 and 143 respectively. Buttons 140 and 141, further details of which will be discussed shortly, are together operative for allowing a user to program circuit board 120 for facilitating operation of fluid transfer device 20 in a plurality of modes of operation, the specific programmable details being conveniently displayed in display 144 electrically coupled to circuit board 120 via electrical interconnection 145. Display 144 is preferably comprised of a conventional LCD display well known to those having ordinary skill, although other displays may be used. As can be seen in FIG. 1, for facilitating ease of access, buttons. 140 and 141, and display 144 are carried by body 22 proximate syringe receiving receptacle 40.

With reference back to FIG. 10, further provided is an encoder 150 electrically coupled to circuit board 120 via electrical interconnection 152. Encoder 150 is operative as a counter for counting the number of revolutions of pinion 65 during a movement, the number of counts corresponding directly to a specific volume of fluid either dispensed from or received within barrel 27 of syringe 24. The number of counts measured by encoder 150 is communicated to circuit board 120 which is operative for regulating the operation of encoder 150 during a specific mode of operation, further details of which will be discussed shortly. Encoder 150, preferably comprised of a conventional rotational encoder, could be replaced with a conventional linear position encoder to obtain the same information or other selected encoder means as desired. In such an application, the linear position encoder would read markings (not shown) on the side of the plunger 25 to indicate the position of plunger 25, and thereby determine the quantity of filled and dispensed fluid. With momentary reference to FIG. 1 and FIG. 2, encoder 150 is housed within housing 151 of body 22.

Reference is now drawn to FIG. 11, which illustrates a simplified block diagram outlining the interrelationship of the elements discussed in combination with FIG. 10 and the Figures associated with FIG. 10. In particular, all of the elements pictured in FIG. 11 are powered by battery 122. Circuit board 120, discussed previously in combination with FIG. 10, is provided with conventional electrical components including a microcontroller 160, an integrated circuit voltage regulator 161, a power switch 162, a full driver bridge 163 having a conventional current sensor 163A, and a direction control switch 164. As can be seen from FIG. 11, battery 122 is directly coupled to voltage regulator 161 and power switch 162. Voltage regulator 161 is coupled intermediate battery 122 and microcontroller 160 and is operative for maintaining the battery voltage provided to microcontroller 160 at an optimum 5 volts for conserving energy and for extending the life of battery 122. Power switch 162 is in turn coupled to full driver bridge 163 and current sensor 163A, of which is then coupled in line motor 71 and encoder 150 respectively. Full driver bridge 163, further details of which will be discussed shortly, is operative for controlling direction, speed, and braking of motor 71. Microcontroller 160 can further be seen as coupled directly to switch 132 which is actuated by pivoting trigger 133, direction control switch 164, buttons 140 and 141, and to display 144.

Microcontroller 160 is selectively programmable for controlling and regulating the operation fluid transfer apparatus 20 in a plurality of programmable modes of operation. Conveniently, display 144 is operative for displaying pertinent operating information so that an operator may be informed as to the operational characteristics of fluid transfer apparatus 20. With respect to the preferred embodiment, these modes of operation include a manual mode, a partial-automatic mode, and an automatic mode.

In the manual mode, operation of fluid transfer device is manual. In particular, to manually operate fluid transfer device, pivoting trigger 133 need only be depressed for actuating switch 132 for commencing selective actuation of plunger 25 in either the reverse direction for extending plunger 25 during a fill operation, or in the forward direction for depressing plunger 25 during a dispense operation. In a particular and more specific aspect, as pivoting trigger 133 is squeezed by the user thereby actuating switch 132, a signal is sent to microcontroller 160 from switch 132 in the form of "on" signal. Microcontroller 160 then sends a signal to power switch 162 which in like manner sends a signal to full driver bridge 163 thereby actuating full driver bridge 163, which in turn actuates motor 71. As with conventional combination speed and direction control switches, such as switch 132, increasing the pull or depression on pivoting trigger 133 will increase the on to off ratio of full driver bridge 163 thereby yielding a faster motor 71 speed. As the speed of motor 71 increases, the faster drive gear 71A rotates and drives driven gear 68 (FIG. 2) which increases the speed at which pinion 65 (FIG. 2) rotates, thereby increasing the speed at which plunger extends or depresses.

When pivoting trigger 133 is depressed in a forward configuration, direction control switch 164, which controls the direction of motor 71 rotation, switches to a forward configuration thereby sending a signal to microcontroller 160 in the form of a "direction control" signal for providing motor 71 rotation in a forward or counterclockwise direction for depressing plunger 25. In like manner, when pivoting trigger 133 is depressed in a reverse configuration, direction control switch 164 switches to a reverse configuration thereby sending a signal to microcontroller in the form of a "direction control" signal for providing motor 71 rotation in a rearward or clockwise direction for extending plunger 25. It will be understood that as pivoting trigger 133 is depressed, a signal is sent to microcontroller 160 in the form of a "speed" signal. Furthermore, this "speed" signal, along with the "direction control" signal provided to microcontroller 160 from direction control switch 164, are both sent to full driver bridge 163 in the form of a "pwm control" signal. The "pwm control" signal sent to full driver bridge 163 corresponds to a power and motor 71 control signal for directing full driver bridge 163 to operate motor 71 in a specific direction and further at a specific speed.

In the manual mode, display 144 is operative for providing a continuous display of plunger 25 position, which is directly related to rotational movement of pinion 65. The position of plunger 25 is directly related to the volume of fluid, usually measured in milliliters or cubic centimeters, either dispensed from syringe 24 during a dispense operation or received by syringe 24 during a fill operation. As has been herein discussed, encoder 150 monitors the rotation of pinion 65 for indirectly monitoring the fluid volume, the information of which is communicated directly to microcontroller 160 in the form of an "encoder input" signal.

In order to switch fluid transfer apparatus 20 to the manual mode, to the partial automatic mode, or to the automatic mode, button 140, which corresponds to a system mode button, is not only operative for switching on the fluid transfer apparatus 20, but is also operative for allowing a user, through the pressing of button 140, to toggle between and select a desired mode of operation until the desired mode is displayed in display 144. Once the manual mode has been selected and "Manual" is displayed in display 144, the signal being received by microcontroller 160 from button 140 being in the form of a "set #1" signal, a user may commence operation of fluid transfer apparatus 20 in the manual mode. However, button 140 need not be pressed prior to operating fluid transfer apparatus 20 in the manual mode. Merely actuating switch 132 with pivoting trigger 133 is enough for commencing operation of fluid transfer apparatus in the manual mode of operation. In the manual mode, when plunger 25 is positioned in the fully dispensed or forward position, button 141, which corresponds to a memory/reset button, may be pressed for recalibrating the linear position of plunger 25 to zero prior to the commencement of a fill and dispense operation, the signal being received by microcontroller 160 from button 141 being in the form of a "set #2" signal.

The next mode of operation of fluid transfer apparatus 20, as previously indicated, is the partial-automatic mode. In the partial-automatic mode of operation, a user may program a dispense or forward movement by first manually dispensing a quantity of solution from syringe 24, with microcontroller 160 then being operative for repeating the dispense movement thereby automatically dispensing the programmed quantity. In particular, and as has been herein previously indicated, in order to select the partial automatic mode, a user need only press button 140 until the partial-automatic mode is displayed in display 144 as indicated in display 144 as "Par-Auto." After the partial-automatic mode has been selected, the user may then manually uptake a desired quantity of solution using pivoting trigger 130 as previously discussed in combination with the manual mode. After pressing button 141 to recalibrate the linear position of plunger 25 to zero and to further signify the beginning of a dispense movement, the user may then, using pivoting trigger 133, manually perform a dispense movement, thereby dispensing a desired volume of fluid, the volume of which is displayed in display 144. After releasing pivoting trigger 133 and pausing for a period of time, herein preferably being a period of about one second, microcontroller 160 memorizes the dispense movement as received from encoder 150 in the form of the encoder input herein previously discussed. Once microcontroller 160 has memorized the dispense movement, it may only be erased by pressing button 140, which clears the memory and resets fluid transfer apparatus to the manual mode of operation. Furthermore, when fluid transfer apparatus 20 is off, and button 140 is pressed to turn it on, the fluid transfer apparatus 20 is set to the manual mode of operation with plunger 25 calibrated to a zero plunger position.

Continuing with the descriptive analysis of the partial-automatic mode of operation, after a dispense movement has been memorized by microcontroller 160, pivoting trigger 133 may then be depressed in the forward position for initiating a programmed dispense movement. During the programmed movement, pivoting trigger 133 is bypassed and microcontroller 160 repeats the specific programmed dispense movement. During the programmed movement, pivoting trigger 133 may be released or held in a depressed position. To begin the next programmed movement in the partial-automatic mode, pivoting trigger 133 need only be depressed in the forward position after the prior movement has been completed. If pivoting trigger 133 has been held in the depressed position, it must be released and then depressed in order to initiate consecutive movements. When syringe 24 is empty, it may be refilled manually to begin another series of programmed operations, with memory being unaffected by reverse operation. However, microcontroller 160 automatically switches to the manual mode of operation and clears memory if plunger 25 remains fully dispensed with no control input for certain period of time, preferably 20 seconds.

The final mode of operation is the automatic mode of operation, which allows a user to program a complete fill and dispense movement by first performing the movement manually. The movement is then stored in memory in microcontroller 160 and automatically repeatable at the discretion of the operator. As has been herein indicated in combination with the above description dealing with the partial-automatic mode of operation, a program or programmed movement may be aborted by pressing button 140. When a program or programmed movement is aborted, memory is cleared and microcontroller 160 is toggled to the manual mode of operation. In the automatic mode, as in the manual mode and the partial-automatic mode, the total number of fill and dispense movements, including the movement or movements used to program microcontroller 160, along with the volume of fluid filled and dispensed, is displayed by display 144.

To operate fluid transfer apparatus 20 in the automatic mode of operation, fluid transfer apparatus 20 must first be switched to the automatic mode by pressing button 140 until "Auto" is displayed by display 144. Upon switching to the automatic mode, microcontroller 160 is ready to accept a fill and dispense operation into memory. In particular, using pivoting trigger 130 for actuating switch 132, a fill and dispense operation is first commenced manually by the user. Upon completion of the fill and dispense operation, pivoting trigger 133 is released and, after a period of time, preferably one second, microcontroller 160 automatically memorizes the fill and dispense operation. It will be understood that in the partial-automatic mode and the automatic mode, corrections in a movement may be commenced within the one second window, and microcontroller 160 will set memory only after one full second after the last control input.

After a fill and dispense operation has been memorized by controller 160, the programmed movement may be commenced. To initiate a programmed movement in the automatic mode of operation, pivoting trigger 133 is depressed in the reverse position actuating switch 132. As a result, fluid transfer apparatus 20 will automatically uptake solution according to the programmed fill movement and stop. To then dispense the solution from syringe 24, pivoting trigger 133 is then released and then depressed in the forward position thereby actuating switch 132. Fluid transfer apparatus 20 will then automatically dispense the solution according to the programmed dispense movement and stop. To initiate subsequent programmed movements, pivoting trigger 133 may be selectively released and depressed, as previously described, at the end of each programmed fill and dispense movement.

In the automatic mode, the total number of programmed movements completed, i.e., complete fill and dispense cycles, are displayed by display 144, the signal provided from microcontroller 160, as with the manual and partial-automatic modes of operation, to display 144 being in the form of a "display" signal. To reset the number of programmed movements completed to zero, one need only press button 141. In the automatic mode, pressing button 141 has no affect on memory, and programmed movements may be continued after the number of programmed movements is set to zero. As has been herein previously indicated, a program or programmed movement in the automatic mode of operation may be aborted by pressing button 140, which clears memory in the microcontroller 160 and resets microcontroller 160 to the manual mode of operation. It will be understood that memory residing in the partial-automatic or automatic modes of operation is cleared when fluid transfer apparatus is switched to a different mode of operation.

In operation, fluid transfer apparatus 20 prevents fatigue of an operators hands due to the automatic depression and extension of plunger 25 by drive assembly 63. Furthermore, since the operator need not touch plunger shaft 33, an entire batch of fluids may be transferred by a single syringe, thereby reducing cost and maintaining aseptic conditions.

As has been herein previously indicated, fluid transfer apparatus 20 is used in conjunction with a selected needle having a selected size, and/or other attachments typical of the application such as tube sets, filters, and the like, of which will be readily understood by those having ordinary skill in the art. Because of the variety of attachments that may be employed with fluid transfer apparatus 20, and due to the fact that many different fluids may also be used having varying viscosity's and flow characteristics, fluid transfer apparatus 20 is provided with an internal safeguard operative for preventing high internal fluid pressure within syringe 24 during either a fill or dispense movement. It will be readily apparent to those having ordinary skill, that such a safeguard is desirable because high internal fluid within a syringe can cause not only damage to an attachment, but may also lead to denigration of the fluid being transferred into and out of the syringe. Accordingly, it is desirable to provide adequate motor 71 dispense speed, i.e., flow rate, with large orifice attachments, while avoiding unacceptably high internal fluid pressure within syringe 24 with small-orifice attachments or high-resistant filters.

Accordingly, in order to solve this problem of providing adequate flow rate without causing damage to the attachments or to the fluid, microcontroller 160 utilizes current sensing as an indirect measure of internal fluid pressure within syringe 24. With respect to the instant application, of which will be understood to those having ordinary skill in the art, motor 71 speed is proportional to voltage, and motor 71 torque is proportional to electric current. As motor 71 torque increases, the amount of electric current consumed by motor 71 also increases. Furthermore, motor 71 torque corresponds directly with plunger 25 driving force, the driving force of plunger 25 thereby determining internal fluid pressure or vacuum within syringe 24 during a dispense or fill movement respectively. In other words, the internal fluid pressure within syringe 24 is directly proportional to plunger 25 driving force, which is the product of motor 71 torque. However, it will be understood by those having ordinary skill that as motor 71 speed increases, motor 71 torque decreases. Thus, at a given voltage, motor 71 torque and the electric current consumed by motor 71 increase directly in proportion to load. Yet, as motor 71 speed increases, motor 71 torque declines, and as motor 71 speed is reduced through greater load, motor 71 torque increases in proportion. When flow is restricted due to the characteristics of the attachment and/or the characteristics of a selected fluid/solution, motor 71 slows down while motor 71 torque and current consumption increase. At some point during a given fill or dispense movement, a balance is achieved in the fluid transfer apparatus 20 wherein motor 71 torque, motor 71 speed, current consumption, and the flow rate of the fluid are in equilibrium. However, at this equilibrium state, the internal fluid pressure within syringe 24 may be too high.

Accordingly, current sensor 163A operates as a sensor means for sensing the current consumption of motor 71 and communicating the current consumption information to microcontroller 160 in the form of a "current sense" signal, although other sensor means may be suitably employed. Thus, during a dispense operation, when the rate of current consumption by motor 71 exceeds a predetermined value as sensed by current sensor 163A, which in the instant application would be the dispense current-limit defined as the rate of current consumption proportional to either the maximum allowable pressure of a specific attachment, or the maximum allowable internal fluid pressure allowable by whatever fluid is being dispensed from syringe 24, whichever is lower, microcontroller 160 then limits that amount of current delivered to motor 71 through full driver bridge 163, regardless of how much the operator depresses pivoting trigger 133, thereby controlling the speed of plunger 25 as it travels through barrel 27 during a dispense movement. Therefore, fluid transfer apparatus 20 allows the operator to control motor 71 speed with low flow-resistant attachments through the use of pivoting trigger 133 and switch 132, yet with high flow-resistant attachments, automatically limits internal fluid pressure within syringe 24 for inhibiting damage to the attachment and for further inhibiting damage to the fluid/solution.

Consistent with the foregoing, during a fill operation, plunger 25 is retracted or extended in order to create a vacuum within barrel 27. If plunger 25 is retracted too rapidly, air may be drawn past piston 31 and into that portion of barrel 27 where fluid resides, thereby resulting in inaccurate intakes of fluid. Current sensor 163A may be configured to sense current consumption during fill operations. Thus, during a fill operation, when the rate of current consumption by motor 71 exceeds a predetermined value as sensed by current sensor 163A, which in the instant application would be the rate of current consumption proportional the maximum vacuum allowable within barrel 27, or the fill current-limit, microcontroller 160 then limits that amount of current delivered to motor 71 through full driver bridge 163, regardless of how much the operator depresses pivoting trigger 133, thereby controlling the speed of plunger 25 as it travels through barrel 27 during a fill movement. Therefore, fluid transfer apparatus 20 allows the operator to control motor 71 speed through the use of pivoting trigger 133 and switch 132, yet with high flow-resistant attachments, automatically limits the internal vacuum within syringe 24. With respect to the instant invention, normally the fill current-limit is set at roughly half the dispense current-limit.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A fluid transfer apparatus comprising:
   a syringe having a barrel for holding fluid;
   a plunger receivable within said barrel;
   a body for holding said syringe;
   a drive assembly having a power source, said drive assembly for actuating said plunger in a fill operation and a dispense operation;
   control means for selectively controlling said drive assembly in a plurality of selectable modes of operation; and
   sensor means for controlling the amount of current supplied to said drive assembly during operation thereof for inhibiting a fluid pressure within said barrel from exceeding a predetermined fluid pressure level during said dispense operation, and for controlling the amount of current supplied to said drive assembly during operation thereof for inhibiting a vacuum within said barrel from exceeding a predetermined vacuum level during said fill operation.

2. The fluid transfer apparatus of claim 1, wherein said drive assembly includes:
   a plunger gear carried by said plunger;
   a pinion mounted in meshing relation with said plunger gear; and actuator means for rotating said pinion in a forward direction for depressing said plunger, and a rearward direction for extending said plunger.

3. The fluid transfer apparatus of claim 2, wherein said actuator means is an electric motor.

4. The fluid transfer apparatus of claim 2 wherein said control means includes:

a switch operative for actuating said drive assembly for depressing and extending said plunger; and a microcontroller coupled to said switch and to said actuator means, said microcontroller being selectively programmable to said modes of operation.

5. The fluid transfer apparatus of claim 4, wherein said control means further includes a trigger for operating said switch.

6. The fluid transfer apparatus of claim 4, wherein said body includes:

a syringe receiving receptacle having an outlet end, and a rearward end.

7. The fluid transfer apparatus of claim 6, wherein said barrel of said syringe is receivable within said syringe receiving receptacle, said barrel being movable within syringe receiving receptacle between an unsecured position and a secured position.

8. The fluid transfer apparatus of claim 7, wherein said barrel further includes a gripping flange extending one end.

9. The fluid transfer apparatus of claim 8, wherein said syringe receiving receptacle further includes a slot for receiving said gripping flange proximate said rearward end.

10. The fluid transfer apparatus of claim 9, wherein said body further includes:

a handle for containing said actuating means extending downwardly proximate said rearward end, wherein said handle terminates with a lower housing for containing said microcontroller.

11. The fluid transfer apparatus of claim 1, wherein said modes of operation include a manual mode, a partial automatic mode, and an automatic mode.

12. The fluid transfer apparatus of claim 1, wherein said sensor means includes a current sensor.

13. The fluid transfer apparatus of claim 1, further including a display for displaying information pertaining to said modes of operation.

14. The fluid transfer apparatus of claim 2, further including a locking pin detachably engagable with said body for urging said plunger gear in engagement with said pinion.

15. A fluid transfer apparatus comprising:

a syringe having a barrel;

a plunger receivable within said barrel;

a body for holding said syringe, said barrel being movable between a locked configuration an unlocked configuration;

a drive assembly having a power source, said drive assembly for actuating said plunger in a fill operation and a dispense operation; and sensor means for controlling the amount of current supplied to said drive assembly during operation thereof for inhibiting a fluid pressure within said barrel from exceeding a predetermined fluid pressure level during said dispense operation, and for controlling the amount of current supplied to said drive assembly during operation thereof for inhibiting a vacuum within said barrel from exceeding a predetermined vacuum level during said fill operation.

16. The fluid transfer apparatus of claim 15, wherein:

said body includes a barrel cavity having a barrel cavity width, and spaced apart upper lips defining a lip width therebetween, and said barrel includes a greatest width slightly smaller than said barrel cavity width but larger than said lip width, and a lesser width slightly smaller than said lip width, said lesser width being received in said barrel cavity through said lip width, whereupon rotation of said barrel from said unlocked configuration engages said greatest width with said barrel cavity width thereby securing said barrel within said barrel cavity in said locked configuration.

17. A fluid transfer apparatus in combination with a syringe having a plunger and a barrel for receiving said plunger, said fluid transfer apparatus comprising:

a body for holding said syringe;

a drive assembly for actuating said plunger in a fill operation and a dispensing operation, said drive assembly including a plunger gear carried by said plunger and a piston mounted in meshing relation with said plunger gear; and plunger lock means for selectively detachably engaging the plunger to said body in a locked configuration and for selectively detachably engaging said plunger to said drive assembly.

18. The fluid transfer apparatus of claim 17, wherein said plunger lock includes:

engagement elements of an engagement set, said engagement elements being detachably engagable to complement engagement elements of said engagement set carried proximate said body relative said plunger.

19. The fluid transfer apparatus of claim 18, wherein said engagement elements include a pair of laterally extending tongue elements each having a protrusion extending outwardly therefrom.

20. The fluid transfer apparatus of claim 19, wherein said complemental engagement elements include a pair of grooves each having a notch formed therein, said tongue elements being received within said grooves, said protrusions correspondingly received within said notches respectively for detachably engaging said plunger lock to said body in said locked configuration.

21. The fluid transfer apparatus of claim 20, wherein said plunger lock is substantially U-shaped.

22. What is claimed is a fluid transfer apparatus for use in combination with a syringe having a plunger and a barrel for receiving said plunger, said fluid transfer apparatus including:

a syringe having a plunger and a barrel for receiving said plunger;

a body for holding said syringe and including a barrel cavity having a barrel cavity width and spaced-apart upper lips defining a lip width therebetween;

said barrel further including a greatest width slightly smaller than said barrel cavity width but larger than said lip width, and a lesser width slightly smaller than said lip width, said lesser width being received in said barrel cavity through said lip width, whereupon rotation of said barrel from said unlocked configuration engages said greatest width with said barrel cavity width thereby securing said barrel within said barrel cavity in said locked configuration; and a drive assembly for actuating said plunger in a fill operation and a dispense operation.

* * * * *